United States Patent

Campbell et al.

[11] Patent Number: 5,877,472
[45] Date of Patent: Mar. 2, 1999

[54] SYSTEM FOR LASER-WELDING COMPONENTS OF AN IMPLANTABLE DEVICE

[75] Inventors: Arthur A. Campbell, Stevenson Ranch; Stephen M. Jones, Canyon Country; Jeffrey L. Pennala, Long Beach, all of Calif.

[73] Assignee: Pacesetter, Inc., Sylmar, Calif.

[21] Appl. No.: 605,439

[22] Filed: Feb. 22, 1996

[51] Int. Cl.⁶ .................................................. B23K 26/00
[52] U.S. Cl. ...................................... 219/121.64; 439/866
[58] Field of Search .................... 219/121.63, 121.64, 219/121.6; 439/866, 874, 880; 174/94 R; 607/36

[56] References Cited

U.S. PATENT DOCUMENTS

| | | | |
|---|---|---|---|
| 3,665,367 | 5/1972 | Keller et al. | 439/866 |
| 4,560,856 | 12/1985 | Miller et al. | 219/121.63 |
| 4,687,264 | 8/1987 | Shuey | 439/880 |
| 5,067,903 | 11/1991 | Szyszkowski | 439/55 |
| 5,103,818 | 4/1992 | Maston et al. | 128/419 P |
| 5,191,701 | 3/1993 | Espenhain | 219/121.64 |
| 5,235,742 | 8/1993 | Szyszkowski | 29/856 |
| 5,282,841 | 2/1994 | Szyszkiwski | 607/36 |
| 5,300,755 | 4/1994 | Nishitani et al. | 219/121.63 |
| 5,315,758 | 5/1994 | Ono et al. | 219/121.64 |
| 5,541,365 | 7/1996 | Sugiura et al. | 219/121.64 |
| 5,569,883 | 10/1996 | Walter et al. | 174/94 R |

*Primary Examiner*—Geoffrey S. Evans

[57] ABSTRACT

Particularly applicable to implantable stimulation devices, a system is provided for laser-welding an electrically conductive elongate member, typically a lead, or elongate member, interconnecting operating components of a stimulation device. A bore is formed in a termination component for the slidable reception of the elongate member. Also formed in the termination component is an aperture in communication with the bore and having an axis which extends in a direction transverse that of the axis of the bore. The elongate member is positioned so it extends through the bore in the termination component and is thereby coplanar with and intersects the axis of the aperture. Thereupon, a laser beam, which may be from a pulse laser, is directed transversely of the elongate member through the aperture in the termination component and onto the elongate member to simultaneously melt the elongate member and the termination component in the region of the aperture and create a homogeneous mix of the molten material of both the elongate member and the termination component within the aperture. Then, operation of the laser beam is discontinued to allow solidification of the homogeneous mix of the molten material within the aperture to thereby achieve a welded connection between the elongate member and the termination component. The aperture in the termination component must be large enough to allow the laser beam to pass therethrough yet small enough to allow the melt of the rim of the aperture and the elongate member simultaneously.

17 Claims, 3 Drawing Sheets

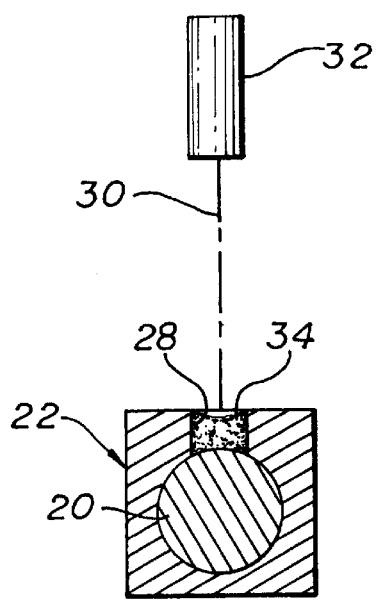
FIG. 5
FIG. 6
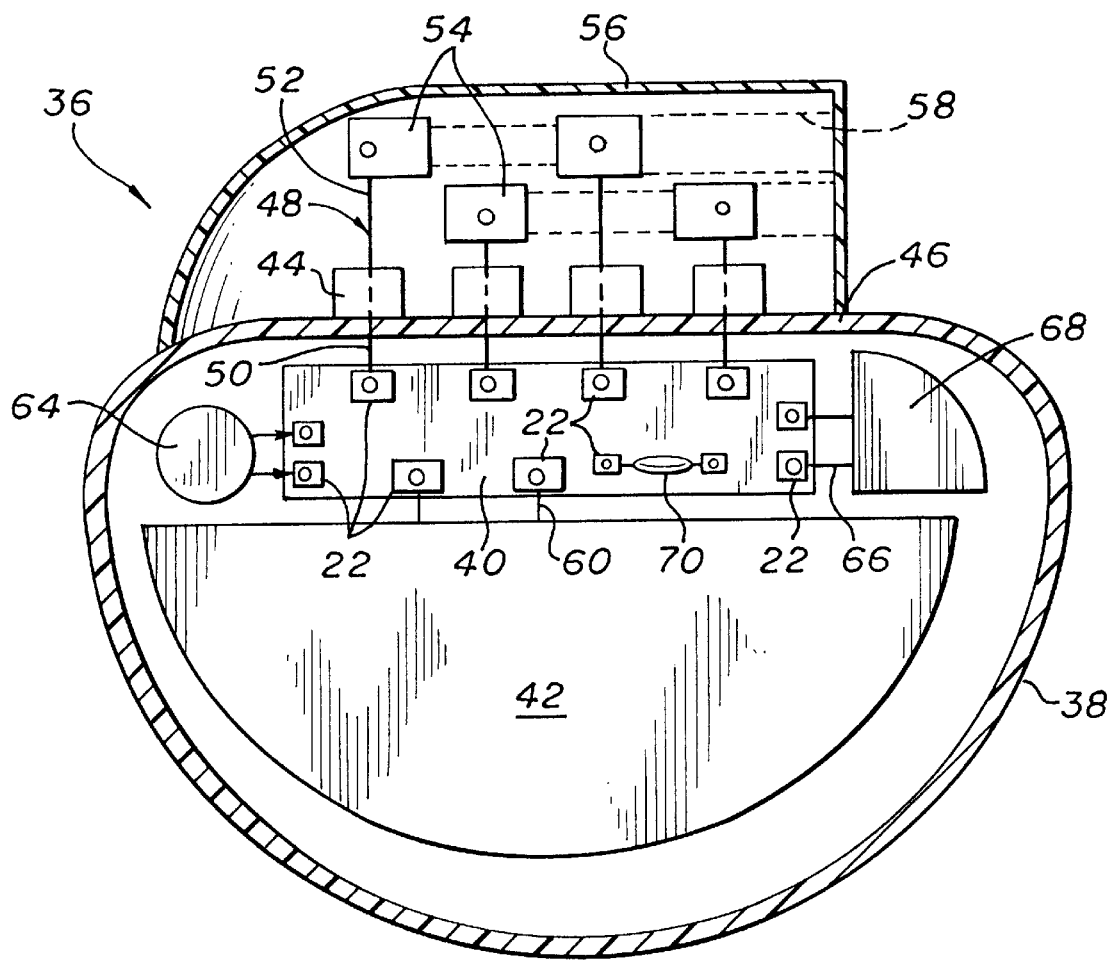

SYSTEM FOR LASER-WELDING COMPONENTS OF AN IMPLANTABLE DEVICE

FIELD OF THE INVENTION

This invention relates generally to improvements in a technique for laser-welding small size wire and connectors. More particularly, this invention relates to a novel technique for conductively interconnecting electrical components in an implantable stimulation device or the like.

BACKGROUND OF THE INVENTION

Implantable stimulation devices of the type having electrical circuit components are well known in the medical arts. In one particularly common form, the implantable device comprises a pacemaker unit having an appropriate electrical power supply and related control circuitry for use in electrically stimulating a patient muscle, such as the heart. Such pacemaker units commonly include an hermetically sealed case or housing within which the power supply and control circuitry are protectively encased, in combination with one or more conductive pacemaker leads extending from the housing to the selected muscle structure within the patient. Feedthrough terminals on the pacemaker housing accommodate hermetically sealed passage of electrical conductors to the housing exterior for appropriate connection to the pacemaker lead or leads, typically through the use of so-called connector blocks having set screws or the like for secure lead attachment. The connector blocks and associated feedthrough conductors disposed externally of the pacemaker housing are commonly encased within an hermetically sealed head structure, such as an insulative head of cast epoxy or the like.

In the past, considerable research and development activity has focused upon the design of feedthrough terminals for permitting pacing signals to be transmitted from the hermetically sealed unit housing. Similarly, significant efforts have been directed toward the design of pacemaker lead connector blocks for obtaining a secure yet hermetically sealed electromechanical connection to pacemaker leads. However, comparatively little attention has been directed to the design of conductors and related installation methods for electromechanically interconnecting the feedthrough terminals with the associated lead connector blocks. To the contrary, available pacemaker units have predominantly utilized elongated wires extending from the feedthrough terminals and individually shaped by bending for appropriate connection by welding or the like to the associated connector blocks. Unfortunately, the close working space provided in a desirably compact implantable device makes this wire bending and shaping procedure both tedious and time consuming. Moreover, in pacemaker units having multiple feedthrough terminal conductors, significant attention and skill are required to maintain the conductor wires in sufficiently spaced array to avoid short circuit failures during pacemaker unit operation.

Recently, there have been significant improvements in devices and methods for electrically interconnecting feedthrough terminals with lead connector blocks in a heart pacemaker unit or other implantable stimulation device, particularly with respect to permitting the desired electrical interconnections to be made quickly and easily with multiple conductors arranged and maintained in spaced relation to prevent short circuit failures. Such improvements are exhibited by the commonly-assigned U.S. Pat. Nos. 5,282,841; 5,235,742; and 5,067,903 to Szyszkowski. As disclosed in those patents, a ribbon conductor set is provided for facilitated electrical connection of feedthrough terminals and lead connector blocks in an implantable stimulation device, such as a heart pacemaker unit or the like. The ribbon conductor set comprises a plurality of conductor ribbons formed as a set in predetermined number, spacing, and geometry to extend between multiple conductors at one or more feedthrough terminals and a plurality of lead connector blocks individually associated with the feedthrough conductors. The conductor ribbons are adapted for installation as a group into a pacemaker unit, and in an orientation which accommodates relatively simple connection to the feedthrough terminals and connector blocks by spot welding or the like.

The commonly used form of welding which has heretofore been satisfactory for implantable stimulation devices has been resistance welding which unfortunately is operator dependent with many variables including electrode wear, force, and voltage. The inventors and others have come to recognize that laser-welding would be desirable for joining small diameter wire to electrodes and connectors, notwithstanding the fact that resistance welders are less expensive than laser welders.

In many instances, present laser weld design concepts for joining small diameter wire (or rod) to electrodes and connectors cannot be used to reliably produce a joint. Components made from dissimilar materials having different melting temperatures, normal component fabrication variability, insignificant thermo mass inherent with certain components, imprecise component alignment during assembly, and unlike materials with distinctly different melting temperatures, are major factors that affect the reliability and repeatability of weld connections using conventional design concepts.

Typical of more recent developments in this regard is the commonly-assigned U.S. Pat. No. 5,103,818 to Maston et al. In this instance, an arrangement is provided which enables the rapid and effective termination of electrical junctions, also for an implantable stimulation device. In this instance, a circuit board supporting electronic circuitry is receivable in a housing for the medical device and is provided with a plurality of female connectors on its outer surface positioned and shaped to receive and guide male components into mating abutting engagement therewith. When the male components and the female connectors are in abutting engagement, they are fusion welded as by a laser or electron beam.

SUMMARY OF THE INVENTION

It was in light of the prior art, as just related, that the present invention was conceived and has now been reduced to practice. Particularly applicable to implantable stimulation devices, a system is provided by the present invention for laser-welding an electrically conductive elongate member, typically a lead, or elongate member, interconnecting operating components of a stimulation device. A bore is formed in a termination component for the slidable reception of the elongate member. Also formed in the termination component is an aperture in communication with the bore and having an axis which extends in a direction transverse that of the axis of the bore. The elongate member is positioned so it extends through the bore in the termination component and is thereby coplanar with and intersects the axis of the aperture. Thereupon, a laser beam, which may be from a pulse laser, is directed transversely of the elongate member through the aperture in the termination component and onto the elongate member to simultaneously melt the elongate member and the termination component in the region of the aperture and create a homogeneous mix of the molten material of both the elongate member and the termination component within the aperture. Then, operation of the laser beam is discontinued to allow solidification of the homogeneous mix of the molten material within the aperture to thereby achieve a welded connection between the elongate member and the termination component. The aperture in the termination component must be large enough to allow the laser beam to pass therethrough yet small enough to allow the melt of the rim of the aperture and the elongate member simultaneously.

The thrust for the present invention was the intention of developing a superior easier and cost effective method of making electrical connections for implantable stimulation devices including hybrid contact pads, connector blocks, and lead assemblies.

Prior art electronic connections for implantable medical devices are currently made by means of solder and/or resistance weld connections. Hybrid connections to implantable device outputs are typically made with the use of flex circuitry connections. Such connections require extremely labor intensive processes which are typically performed under a microscope, are costly, and are difficult to automate.

Noted above, commonly-assigned U.S. Pat. No. 5,103,108 to Maston et al. teaches using a pin-and-socket interconnect scheme with fusion welding, which is described as requiring little tooling or fixturing. The disadvantages of this technique, however, include: (a) not being able to direct the melt; b) noncontainment of the wire/component to be welded; and (c) material loss.

The present invention is directed toward a KOVAR® pad with a through-hole for reception of a wire lead; and employing laser-welding to join the wire lead to the pad. KOVAR® is a registered trademark for an alloy of iron and nickel, cobalt and manganese. The range of compositions may be 23%–30% nickel, 17%–30% cobalt, and 0.6%–0.8% manganese and is particularly desirable in electronic applications because of the fact that its coefficient of expansion is practically identical with all commercial hard glasses. In manufacturing of implantable stimulation devices, such a technique would eliminate the flex circuitry completely.

This present invention is not limited to KOVAR® pads on hybrids, but can apply the structure and weld process to other components, such as connector blocks, and/or lead electrodes to allow direct attachment from feedthrough wires to connector assemblies, thereby eliminating conductor ribbons, forming tools, and the like, of lead windings to electrode tips. This technique has the potential of becoming an industry standard for many laser-welding applications, in large part because it is visible to the naked eye without requiring destructive testing of the parts.

The structure of the invention is based on the need to minimize the interconnect methodology within implantable stimulation devices. The invention serves to enhance the melt characteristic required when using the laser-welding process. When laser-welding miniature components, the materials to be joined must be effectively designed to accommodate the process or else in the resulting melt process, a drastic reduction in material loss and/or strength will occur. The weld process can only be achieved with the intermingling of the metals needing to be joined inasmuch as there is no filler material in laser-welding, in general, and in this process, in particular.

A particular benefit of the present invention resides in the concept of capturing the material to be joined while both utilizing and directing the melt flow to increase weld strength, reliability and repeatability.

The invention addresses the concern that if the material to be welded is to be captured or restricted in order to minimize melt flow, the result would be a maximizing of material strength while minimizing material depreciation, that is, melt. With the miniature diameters of components used in implantable stimulation devices, this problem becomes compounded. If too much melting occurs, and the wire diameter is minimized due to reflow, material strength is compromised as a result of such reduction in wire diameter.

Small diameter wire leads must be captured accurately. Tooling to capture miniature components requires a substantial amount of design and machine operating time. However, as connections are made utilizing the present invention: (a) a wire lead is held in place, eliminating tooling; (b) melt flow is restricted; (c) the only outlet for the melt is in the direction of the laser beam, thus creating a "weld rivet"; and (d) depending on the diameter of the lead wires and components to be joined, the insertion or diameter can be adjusted to accommodate varying sizes. The shape of the component may be of any configuration, for example, round, rectangular, spherical, D-shaped, square, and the like.

Current configurations of all known connector assemblies require two connections to make a single electrical contact. With a connector block or connector assembly employing the present invention, conductor ribbons, forming tools, weld fixtures, and the like can be eliminated.

Whether implantable stimulation devices utilize flex cables for interconnections or wire leads which are resistance welded and/or soldered to hybrid posts, KOVAR® pads, and/or connector blocks), the hardware requiring interconnections designed in accordance with the present invention will eliminate redundancy. Hardware, such as flex cables, conductor ribbons, tooling, and the like, can be eliminated while improving reliability through laser-welding. As a result, operator dependent operations, such as resistance welding and/or soldering, are eliminated.

KOVAR® pads employed for purposes of the invention would utilize current bonding technologies for adherence to the hybrid or other substrate. In those constructions utilizing dual hybrids, the hybrids could be designed to accommodate this technique as part of the interconnect scheme in joining the two hybrids. In this situation, one hybrid could accommodate the proposed pad configuration, while the mating hybrid is interfaced through a pin. By inserting the connector pins into mating pads, both hybrids could be laser-welded thereby joining the hybrids together. Advantages and novel features of the invention include:

(a) self fixturing, that is, no tooling is required resulting in a significant cost savings;
(b) ease of manufacture and inspection;
(c) reliability of welds within product;
(d) one laser-welder with components in the configuration of the invention can replace a minimum of eight (8) resistance welders, with the accompanying need for weld schedules/operations/inspections, all steps currently utilized in existing implantable stimulation devices; and
(e) replacement of crimping as method of wire lead attachment which increases reliability, throughput and repeatability.

Present or future products could typically incorporate the invention into:

(a) direct connections from feedthrough to connector blocks and/or connectors;

(b) lead windings to electrode tips;

(c) reed switch to KOVAR® pad;

(d) feedthrough to hybrid;

(e) battery terminals to hybrid;

(f) ground wire to case; and (g) coil, piezo and accelerometer connections.

Accordingly, a primary object of the present invention is to provide a technique for reliably welding small diameter wire leads to electrical components.

Another object of the invention is to provide such a novel welding technique which comprises the steps of forming a bore in a termination component for the slidable reception of a wire lead, forming in the termination component, an aperture in communication with the bore and having an axis which extends in a direction transverse that of the axis of the bore, positioning the wire lead so it extends through the bore, directing a laser beam transversely of the wire lead through the aperture in the termination component and onto the wire lead to simultaneously melt the wire lead and the termination component in the region of the aperture and create a homogeneous mix of the molten material of both the wire lead and the termination component within the aperture, then discontinuing operation of the laser beam to allow solidification of the homogeneous mix of the molten material within the aperture to thereby achieve a welded connection between the wire lead and the termination component.

Still another object of the invention is to provide such a process in which the laser beam is provided by a pulse laser.

Yet another object of the invention is to provide such a process in which the aperture is formed large enough to allow the laser beam to pass therethrough, yet small enough to allow the melt of the rim of the aperture and the elongate member simultaneously.

Other and further features and advantages of the present invention will become more apparent from the following detailed description, taken in conjunction with the accompanying drawings which illustrate, by way of example, the principles of the invention. Throughout the specification, like numerals refer to like parts.

BRIEF DESCRIPTION OF THE DRAWINGS

The accompanying drawings illustrate the invention:

FIG. 5 is a cross-section view of the termination component and elongate member combination being subjected to a laser-welding procedure;

FIG. 6 is a diagrammatic side elevation view of an implantable stimulation device utilizing the electrical connection technique of the invention;

DETAILED DESCRIPTION OF THE PREFERRED EMBODIMENT

Figure 1:
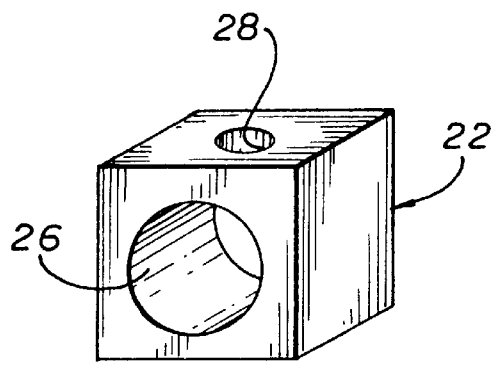
FIG. 1 is a perspective view of a termination component embodying the present invention.
Figure 2:
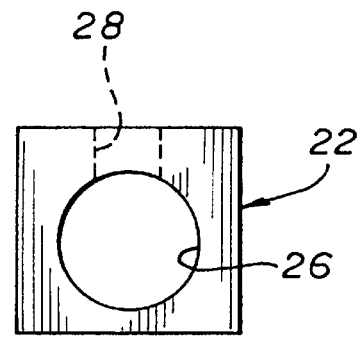
FIG. 2 is a side elevation view, of the termination component illustrated in FIG. 1.

Turn now to the exemplary drawings and initially to FIGS. 1–5 which diagrammatically illustrate a technique, according to the invention, for welding an electrically conductive elongate member 20 to an electrically conductive termination component. In keeping with the invention, the termination component is, typically, although not to be limiting of the invention, a KOVAR® pad mounted on a substrate 24 which may be any component to which the elongate member 20, typically a wire lead, is to be joined. A bore 26 is formed in the termination component 22 for the slidable reception of the elongate member. Also formed in the termination component is an aperture 28 which is in communication with the bore 26 and which has an axis which extends in a direction transverse that of the axis of the bore.

Figure 3:
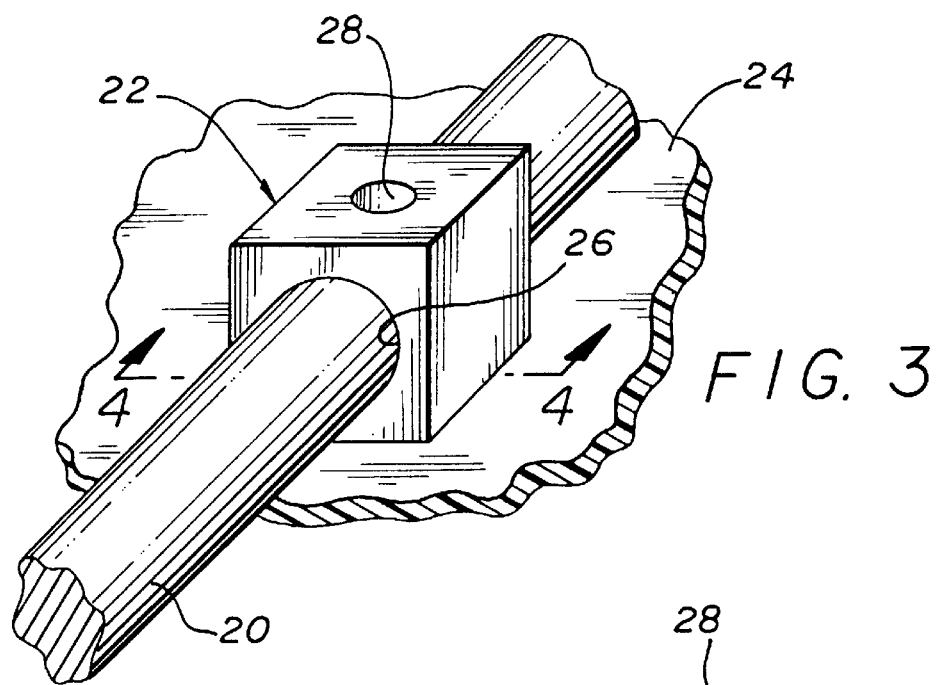
FIG. 3 is a perspective view of the termination component illustrated in FIGS. 1 and 2 shown in combination with a substrate on which it is mounted and an elongate member for attachment thereto.
Figure 4:
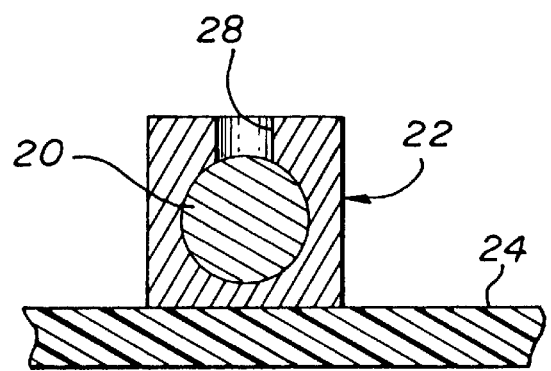
FIG. 4 is a cross-section view taken generally along line 4—4 in FIG. 3.

As seen in FIGS. 3 and 4, the elongate member 20 is inserted into the bore 26 in the termination component and positioned so that it extends through the bore, or at least to the extent that it is coextensive with the aperture 28.

Thereupon, viewing FIG. 5, a laser beam 30 is directed, as from a pulse laser 32 transversely of the elongate member 20 through the aperture 28 in the termination component 22 and onto the elongate member to simultaneously melt the elongate member and the termination component in the region of the aperture and create a homogeneous mix of the molten material of both the elongate member and the termination component within the aperture. It will be appreciated that the aperture 28 must be formed large enough to allow the laser beam 30 to pass unimpeded to the elongate member yet small enough to allow the melt of the rim of the aperture and the elongate member simultaneously.

Operation of the laser beam is then discontinued to allow solidification of the homogeneous mix of the molten material within the aperture 28 to thereby achieve a welded connection between the elongate member and the termination component. When this homogeneous mix becomes solidified, it achieves a welded connection between the elongate member and the termination component and forms a concave weld fillet 34 overlying the former aperture.

FIG. 6 is a diagrammatic view of an implantable stimulation device 36 such as a heart pacemaker embodying the present invention. The device 36 is seen to include a housing 38 which is hermetically sealed when implanted in the body of a patient. The housing is adapted to receive within its confines a circuit board or hybrid 40 with suitable electronic circuitry thereon for operation of the device 36 and a suitable battery 42 for energizing the device. As diagrammatically illustrated in FIG. 6, four sets of feedthroughs 44 extend through a side wall 46 of the housing 38 with adequate insulation to electrically isolate wire leads 48 extending therethrough. Each wire lead 48 extends between proximal and distal ends 50, 52, respectively. The proximal end 50 is attached in the manner of the invention, already described, to an associated termination component or pad 22 fixed on the hybrid 40. The distal end 52 extends to, and is suitably attached to an associated connector block 54. The manner of attachment to the connector block may be conventional or, preferably, in the manner of the invention as well. A casting 56 which is mounted on the housing 38 encapsulates the connector blocks 54 and feedthroughs 44 and serves to prevent body fluids from coming into contact with the wire leads 48. Proximal ends of pacemaker leads (not shown) are received through suitable jack openings in the casting 56 for electrical connection with associated connector blocks 54. The distal ends of the pacemaker leads are suitably attached to the heart of the patient.

Returning to the housing 38, a variety of connections may be seen utilizing the termination components or pads 22 of the invention. For example, wire leads 60 interconnect the battery 42 and the hybrid 40, wire leads 62 interconnect a coil 64 and the hybrid, and wire leads 66 interconnect an accelerometer 68 and the hybrid 40. Also, leads from a reed switch extend between and are connected to opposed pads 22 both fixed on the hybrid 40.

Figure 7:
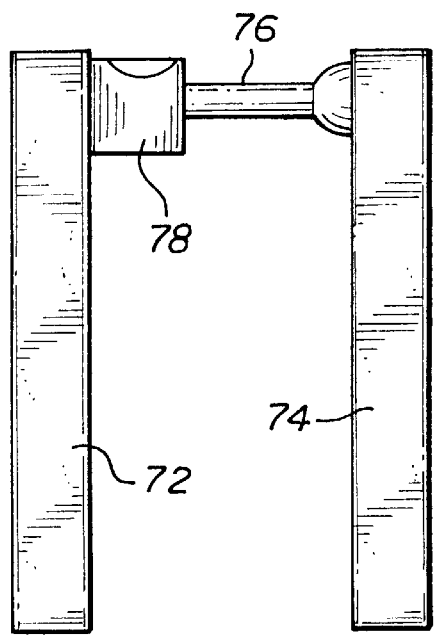
FIG. 7 is a diagrammatic side elevation view of a pair of hybrids electrically interconnected in accordance with the invention.

Consider another instance of the use of the invention, as illustrated in FIG. 7. When utilizing dual hybrids 72, 74 such as in an implantable cardioverter-defibrillator (ICD), the hybrids may be designed to accommodate the technique of the invention as part of the interconnect scheme for joining them together. For example, one hybrid could accommodate the proposed termination component/pad configuration, while the mating hybrid is interfaced by means of a pin. Thus, by inserting connector pins 76 from the hybrid 74 into mating pads 78 of the hybrid 72, both hybrids could be laser welded thus joining them together.

Figure 8:
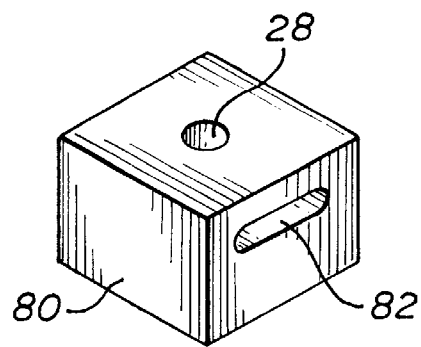
FIG. 8 is a perspective view of a modified termination component embodying the invention.
Figure 9:
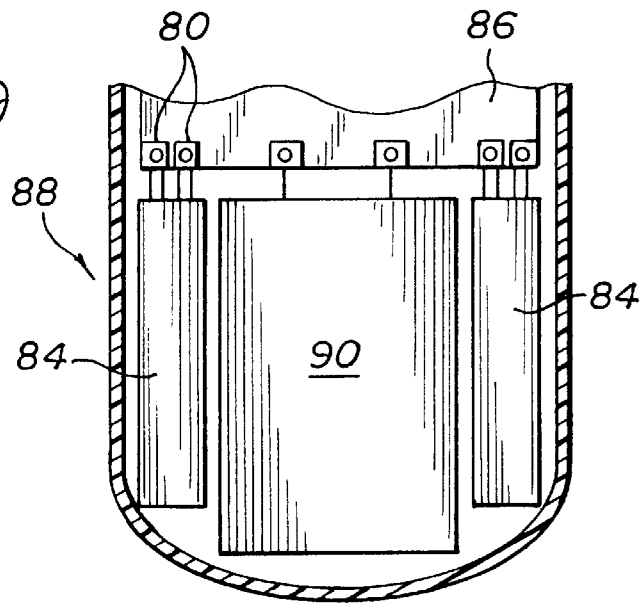
FIG. 9 is a diagrammatic side elevation view of an implantable stimulation device utilizing the modified termination component illustrated in FIG. 8.
Figure 10:
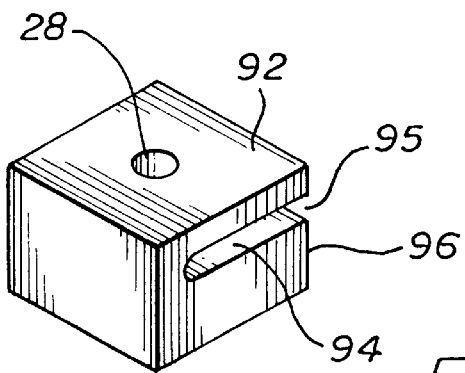
FIG. 10 is a perspective view of a further modified termination component embodying the invention.

In yet another instance, turning to FIG. 8, a modified pad 80 is formed with a slit 82, or elongated bore, which might be desirable for attachment of a capacitor 84 to a hybrid 86 within an implantable stimulation device 88 energized by a battery 90. A further modification of pad 80 is illustrated in FIG. 10 as pad 92 formed with a slit 94 which communicates with an opening 95 in a side wall 96 of the pad. Being coextensive with the slit 94, the opening 95 allows lateral insertion of an elongate member should that be desirable.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A method of welding an electrically conductive elongate member to an electrically conductive termination component comprising the steps of:
   (a) forming in the termination component a bore for the slidable reception lengthwise of the elongate member while constraining the elongate member against movement transverse of its longitudinal axis;
   (b) forming in the termination component an aperture in communication with the bore and having an axis which extends in a direction transverse that of the axis of the bore;
   (c) positioning the elongate member so it extends through the bore in the termination component;
   (d) directing a laser beam transversely of the elongate member through the aperture in the termination component and onto the elongate member to simultaneously melt the elongate member and the termination component in the region of the aperture and create a homogeneous mix of the molten material of both the elongate member and the termination component within the aperture; and
   (e) discontinuing operation of the laser beam to allow solidification of the homogeneous mix of the molten material of step (d) within the aperture to thereby achieve a welded connection between the elongate member and the termination component.

2. A method, as set forth in claim 1, wherein step (d) is performed by a pulse laser.

3. A method, as set forth in claim 1, wherein step (b) includes the step of:
   (f) forming the aperture large enough to allow the laser beam to pass therethrough yet small enough to allow the melt of the rim of the aperture and the elongate member simultaneously.

4. A method as set forth in claim 1, wherein:
   the termination component is a pad mounted on a substrate, the pad being constituted of an alloy of iron and nickel, cobalt and manganese; and
   the elongate member is a wire lead to be joined to the substrate.

5. A method, as set forth in claim 1, including the step of:
   (f) forming in a side wall of the termination component an opening which is coextensive with and communicates with the bore therein to allow lateral insertion into the bore of an elongate member.

6. An electrical connection for an implantable stimulation device comprising:
   an electrically conductive elongate member; and
   an electrically conductive termination component having a bore therein for the slidable lengthwise reception of the elongate member while constraining the elongate member against movement transverse of its longitudinal axis and an aperture in communication with the bore and having a rim and an axis that extends in a direction transverse an axis of the bore;
   wherein the elongate member is received in the bore of the termination component such that it is coplanar with and intersects the axis of the aperture;
   wherein a weld connection is formed by directing a laser beam transversely of the elongate member through the aperture so that the laser beam impinges on the elongate member and on the rim of the aperture to simultaneously melt the rim of the aperture of the termination component and the elongate member and create a homogeneous mix of the material of the elongate member with the material of the termination component within the aperture which, when solidified, achieves a welded connection between the elongate member and the termination component and forms a concave weld fillet overlying the former aperture.

7. An implantable stimulation device, as set forth in claim 6, wherein said termination component has a side wall having an opening therein which is coextensive with and communicates with the bore therein to allow lateral insertion of an elongate member.

8. An implantable stimulation device as set forth in claim 6, wherein:
   the termination component is a pad mounted on a substrate, the pad being constituted of an alloy of iron and nickel, cobalt and manganese; and
   wherein the elongate member is a wire lead to be joined to the substrate.

9. An implantable stimulation device, as set forth in claim 6, wherein said implantable stimulation device is a pacemaker.

10. A method of welding an elongate conductor to a termination component comprising the steps of:
   (a) forming a bore through the termination component for snugly but freely slidably receiving and peripherally enveloping the elongate conductor;

(b) forming in the termination component an aperture in communication with the bore;

(c) positioning the elongate conductor in the bore of the termination component so as to be coextensive with the aperture;

(d) directing a laser beam through the aperture in the termination component and onto the elongate conductor;

(e) dimensioning the aperture so as to be sufficiently large for the laser beam to pass unimpeded to the elongate conductor yet small enough to melt the rim of the aperture and the elongate conductor simultaneously and create a homogeneous mix of the molten material of both the elongate conductor and the termination component within the aperture; and (f) allowing the homogeneous mix of the molten material of step (e) to solidify within the termination component and to solidify within the aperture to thereby create a weld rivet for firmly affixing the elongate conductor to the termination component.

11. A method as set forth in claim 10, wherein the termination component is constituted of an alloy of iron and nickel, cobalt and manganese.

12. A method of welding an elongate conductor to a self-fixturing termination component comprising the steps of:

(a) forming a bore through the termination component for snugly but freely slidably receiving and substantially peripherally enveloping the elongate conductor;

(b) forming in the termination component an aperture in communication with the bore;

(c) positioning the elongate conductor in the bore of the termination component so as to be coextensive with the aperture;

(d) directing a laser beam through the aperture in the termination component and onto the elongate conductor;

(e) dimensioning the aperture so as to be sufficiently large for the laser beam to pass unimpeded to the elongate conductor yet small enough to melt the rim of the aperture and the elongate conductor simultaneously and create a homogeneous mix of the molten material of both the elongate conductor and the termination component within the aperture; and (f) allowing the homogeneous mix of the molten material of step (e) to solidify within the region of the aperture to thereby create a weld rivet for firmly affixing the elongate conductor to the termination component.

13. A method, as set forth in claim 12, wherein step (a) includes the step of:

(g) forming in a side wall of the termination component an opening which is coextensive with and communicates with the bore therein to allow lateral insertion into the bore of an elongate conductor.

14. A self-fixturing termination component for an implantable stimulation device comprising:

an elongated tubular member having a bore therein for snugly but freely slidably receiving and peripherally enveloping an elongate conductor and having an aperture in communication with the bore defined by a rim dimensioned smaller than a laser beam having a finite cross section so that a welded connection is formed by directing a laser beam through the aperture, so that the laser beam impinges on the elongate conductor and on the rim of the aperture to simultaneously melt the rim of the termination component and the elongate conductor and create a homogeneous mix of the material of the elongate conductor with the material of the termination component within the aperture which, when solidified, achieves a welded connection between the elongate conductor and the termination component.

15. A self-fixturing termination component for an implantable stimulation device as set forth in claim 14, wherein the termination component is constituted of an alloy of iron and nickel, cobalt and manganese.

16. A self-fixturing termination component for an implantable stimulation device comprising:

an elongated tubular member having a bore therein for snugly but freely slidably receiving and peripherally substantially enveloping an elongate conductor and having an aperture in communication with the bore defined by a rim dimensioned smaller than a cross section of a laser beam so that a welded connection is formed by directing a laser beam through the aperture, such that the laser beam impinges on the elongate conductor and on the rim of the aperture to simultaneously melt the rim of the termination component and the elongate conductor and create a homogeneous mix of the material of the elongate conductor with the material of the termination component within the aperture which, when solidified, achieves a welded connection between the elongate conductor and the termination component.

17. A self-fixturing termination component for an implantable stimulation device as set forth in claim 16, wherein the termination component has a side wall having an opening therein which is coextensive with and communicates with the bore therein to allow lateral insertion of the elongate conductor.

* * * * *